United States Patent
Coville et al.

(10) Patent No.: US 6,740,240 B2
(45) Date of Patent: May 25, 2004

(54) METHOD AND APPARATUS FOR DIRECTLY SAMPLING A FLUID FOR MICROFILTRATION

(75) Inventors: William E. Coville, Levittown, PA (US); David M. St. Onge, North Wales, PA (US)

(73) Assignee: Bio/Data Corporation, Horsham, PA (US)

( * ) Notice: Subject to any disclaimer, the term of this patent is extended or adjusted under 35 U.S.C. 154(b) by 201 days.

(21) Appl. No.: 10/068,331

(22) Filed: Feb. 6, 2002

(65) Prior Publication Data

US 2002/0084215 A1 Jul. 4, 2002

Related U.S. Application Data

(62) Division of application No. 09/580,987, filed on May 30, 2000, now Pat. No. 6,398,956.
(60) Provisional application No. 60/136,668, filed on May 28, 1999.

(51) Int. Cl.[7] ............................................... B01D 61/00
(52) U.S. Cl. .................. 210/645; 210/651; 210/650; 210/321.75; 422/101; 422/102; 422/104
(58) Field of Search ................................. 210/645, 651, 210/650, 321.75; 422/82, 99, 101, 102, 104.5; 604/411

(56) References Cited

U.S. PATENT DOCUMENTS

| | | |
|---|---|---|
| 3,780,935 A | 12/1973 | Lukacs et al. |
| 3,888,770 A | 6/1975 | Avital et al. |
| RE28,801 E | 5/1976 | Acker et al. |
| 3,963,119 A | 6/1976 | Lukacs et al. |
| 4,096,825 A | 6/1978 | Golias et al. |
| 4,279,860 A | 7/1981 | Smolen |
| 4,342,341 A | 8/1982 | Lee |
| 4,400,353 A | 8/1983 | Meserol et al. |
| 4,452,902 A | 6/1984 | Suovaniemi et al. |

(List continued on next page.)

FOREIGN PATENT DOCUMENTS

WO      Wo 94 12885       6/1994

OTHER PUBLICATIONS

H–Pette® Dispenser, Helena Laboratories Website (brochure date unknown, but trademark registered showing first use in commerce in Nov. of 1993 as shown in attached registration printout from PTO)—Total pp.: 6.

TipTop® Dispenser Caps, Helena Laboratories Website (product on sale in commerce as of Jan. 26, 1987 based on trademark registration pages attached)—Total pp.: 7.

(List continued on next page.)

*Primary Examiner*—Ana M. Fortuna
(74) *Attorney, Agent, or Firm*—Volpe and Koenig, P.C.

(57) ABSTRACT

Filtration cells capable of direct sampling of a fluid from a container and which may be used for microfiltration of both small and large microvolumes of a fluid to be filtered are provided Also a process for directly transferring a fluid to be filtered from a container to a filtration cell is described. The filtration cells have one or more reservoirs and are in communication with fluid in a container to be filtered through a piercing instrument connected to a base and support for a reservoir that receives the fluid to be filtered after it passed across a filter membrane. The filtration cell may then be pressurized and vented to allow fluid to be filtered to reciprocally and tangentially pass across a filter membrane between either a container having a fluid to be filtered and a single reservoir for small volume filtrations or between two reservoirs after pressurizing a fluid to be filtered into the reservoirs from a container using a piercing instrument. Side wells for collecting samples from the bottom up from the filtration cell outlet are also provided as are a process incorporating automated equipment for transferring the container having fluid to be filtered to the piercing point for entry into the filtration cell.

13 Claims, 6 Drawing Sheets

U.S. PATENT DOCUMENTS

| | | | |
|---|---|---|---|
| 4,659,550 A | 4/1987 | Schildknecht | |
| 4,668,636 A | 5/1987 | Ringrose et al. | |
| 4,683,120 A | 7/1987 | Meserol et al. | |
| 4,695,430 A | 9/1987 | Coville et al. | |
| 4,719,087 A | 1/1988 | Hanaway | |
| 4,726,929 A | 2/1988 | Gropper et al. | |
| 4,777,021 A | 10/1988 | Wertz et al. | |
| 4,818,493 A | 4/1989 | Coville et al. | |
| 4,843,017 A | 6/1989 | Oberhardt et al. | |
| 4,902,481 A | 2/1990 | Clark et al. | |
| 4,919,894 A | 4/1990 | Daniel | |
| 4,929,426 A | 5/1990 | Bodai et al. | |
| 4,933,147 A | 6/1990 | Hollar et al. | |
| 4,948,564 A | 8/1990 | Root et al. | |
| 4,961,906 A | 10/1990 | Andersen et al. | |
| 4,970,052 A | 11/1990 | Oberhardt et al. | |
| 4,976,926 A | 12/1990 | Matkovich | |
| 4,988,482 A | 1/1991 | Weston | |
| 5,000,923 A | 3/1991 | Coville et al. | |
| 5,001,417 A | 3/1991 | Pumphrey et al. | |
| 5,004,583 A | 4/1991 | Guruswamy et al. | |
| 5,031,797 A | 7/1991 | Boris et al. | |
| 5,059,394 A | 10/1991 | Phillips et al. | |
| 5,089,229 A | 2/1992 | Heidt et al. | |
| RE33,858 E | 3/1992 | Gropper et al. | |
| 5,106,583 A | 4/1992 | Raysberg et al. | |
| 5,110,724 A | 5/1992 | Hewett | |
| 5,114,859 A | 5/1992 | Kagenow | |
| 5,122,284 A | 6/1992 | Braynin et al. | |
| 5,173,265 A | 12/1992 | Golias et al. | |
| 5,190,666 A | 3/1993 | Bisconte | |
| 5,200,152 A | 4/1993 | Brown | |
| 5,205,989 A | 4/1993 | Aysta | |
| 5,221,519 A | 6/1993 | Wuerschum | |
| 5,250,262 A | 10/1993 | Heidt et al. | |
| 5,252,293 A | 10/1993 | Drbal et al. | |
| 5,254,315 A | 10/1993 | Nurse et al. | |
| 5,258,314 A | 11/1993 | Skerratt | |
| 5,290,517 A | 3/1994 | Samuels et al. | |
| 5,304,350 A | 4/1994 | Meserol | |
| 5,314,663 A | 5/1994 | Mimura | |
| 5,320,808 A | 6/1994 | Holen et al. | |
| 5,336,467 A | 8/1994 | Heidt et al. | |
| 5,352,612 A | 10/1994 | Huber et al. | |
| 5,356,525 A | 10/1994 | Goodale et al. | |
| 5,358,691 A | 10/1994 | Clark et al. | |
| 5,376,313 A | 12/1994 | Kanewske, III et al. | |
| 5,384,093 A | 1/1995 | Ootani et al. | |
| 5,397,026 A | 3/1995 | Mayes | |
| 5,400,923 A | 3/1995 | Golias et al. | |
| 5,591,636 A | 1/1997 | Grass | |
| 5,601,727 A | 2/1997 | Bormann et al. | |
| 5,665,238 A | 9/1997 | Whitson et al. | |
| 5,697,522 A | 12/1997 | Mayes | |
| 5,736,033 A | 4/1998 | Coleman et al. | |
| 5,879,628 A | 3/1999 | Ridgeway et al. | |
| 6,016,712 A | 1/2000 | Warden et al. | |
| 6,146,591 A | 11/2000 | Miller | |
| 6,398,956 B1 * | 6/2002 | Coville et al. | 210/321.75 |

OTHER PUBLICATIONS

Microtainer® Stat Plasma Tubes Product Brochure (product first used in commerce as of May 1970 based on trademark registration pages attached)—Total pp.: 3.

Diff–Sale® Blood Dispenser, Alpha Scientific Website (product first used in commerce Sep. 15, 1993 based on trademark registration pages attached)—Total pp.: 4.

Diff–Sale® Advertisement, Advance (Jan. 1995)—Total p.: 1.

Seg–Safe® Segment Processor, Alpha Scientific Website (product first used in commerce Apr. 1, 1996 based on trademark registration pages attached)—Total pp.: 4.

Proseptor® DBCD, Inc. Website plus background photo of device (product submitted in intent–to–use application on Mar. 17, 1998 based on trademark search pages attached)—Total pp.: 8.

SegMed Blood Tubing Sampling System, NHS Website (product first used in commerce as of Mar. 1989 based on trademark registration pages attached)—Total pp.: 7.

* cited by examiner

METHOD AND APPARATUS FOR DIRECTLY SAMPLING A FLUID FOR MICROFILTRATION

CROSS-REFERENCE TO RELATED APPLICATION

This application is a divisional application of Application No. 09/580,987 filed May 30, 2000 now U.S. Pat. No. 6,398,956, entitled "METHOD AND APPARATUS FOR DIRECTLY SAMPLING A FLUID FOR MICROFILTRATION", which claims the benefit of Provisional Application No. 60/136,668, filed May 28, 1999. The entire disclosures of U.S. application Ser. No. 60/136,668 and U.S. application Ser. No. 09/580,987 as filed are incorporated herein by reference.

BACKGROUND OF THE INVENTION

Microfiltration is known as are filtration cells that produce a filtrate through microfiltration. U.S. Pat. No. 4,818,493 discloses a filtration cell for separating a filtrate from a fluid, such as plasma from blood, by means of microfiltration. U.S. Pat. No. 5,000,923 discloses a particular filtration cell having application in the art of filtering plasma from blood by a microfiltration. U.S. Pat. No. 4,695,430 discloses an automated apparatus for effecting the filtration of biological fluids using a filtration cell of the type disclosed in the aforesaid two patents, and then further processing the cell to analyze the filtrate for various biological aspects, such as blood clotting time.

In recent years, the process of filtering and analyzing the fluid has been further developed to the point where it is full automated. There is, however, a remaining problem; namely the problem of specimen transfer. Present day microfiltration apparatus, such as the apparatus disclosed in the three above-cited patents and improvements thereon, provide a continuous flow operation for obtaining high quality biologic and other samples. Each specimen can be processed in about thirty seconds. Moreover, the capital cost for the equipment is less than alternative equipment for accomplishing the same result. Despite its advantages, such apparatus does not solve all the problems of automation. Current approaches to specimen transfer severely limit automation. Specimen transfer requires precision pumps and rinse solution. All automated specimen processing systems share these problems. This translates into increased equipment costs as well as biohazardous waste transfer and disposal costs. Other costs include operating costs such as reagent fluid, disposable tubing, waste containers and waste transfer and disposal expenses.

Each specimen transfer requires additional time in the process cycle. Specimen transfer takes about 45 seconds to perform using the Bio/Data Corporation MCA 310 which is a present day version of the apparatus disclosed in the three patents cited above. The filtration cycle requires only 17 to 20 seconds. Thus the specimen transfer process, when coupled with the filtration cycle requires about 1 minute. This is a reasonable rate for processing specimens, but the preliminary step of specimen transfer takes almost three quarters of that time. Analysis of the specimen transfer process helps define the problem. The specimen transfer operation may be outlined as follows:

1. Loading the specimen container.
2. Mix specimen
3. Positioning the specimen container at a 30 degree down angle.
4. Indexing the piercing needle up 30 degrees from the horizontal.
5. Driving the needle forward into the specimen tube and pumping out a volume specimen. In the MCA 310, this process occurs in two different sized specimen tubes, however, it would be desirable to carry out this step independent of the size of the specimen tubes.
6. Retracting the needle.
7. Indexing the needle down to a vertical position and then extending the needle into the cell reservoir chamber.
8. Dispensing a volume of specimen into the cell.
9. Retracting the needle.
10. Indexing the needle to a third position.
11. Extending the needle into a rinse chamber and then dispensing a volume of rinse solution greater than the specimen volume.

Moreover, apparatus for performing the transfer operation includes the following:

A rinse solution reservoir.
A precision pump.
A mechanism for mixing the specimen.
A mechanism for articulating the piercing needle.
A waste collection container.

There is a need in the art for a microfiltration cell which minimizes the time associated with specimen transfer and the additional equipment associated therewith and which improves the time associated with use of microfiltration cells. There is also a need in the art for a microfiltration cell which provides further control of specimen and sample handling and the type and volume of samples which may be taken as filtrate from the microfiltration cell. Additionally, there is a need for a microfiltration cell which improves internal specimen handling and removes as much specimen as possible in order to provide either small or large volumes of sample depending on particular applications. The present invention uses a single pressure source and can achieve these advantages such as others as outlined further below in the description of the present invention.

SUMMARY OF THE INVENTION

The invention includes a filtration cell capable of direct sampling of a fluid from a container. The filtration cell comprises a reservoir to receive the fluid to be filtered; a filter membrane capable of filtering the fluid to provide a filtrate, the membrane being operatively associated with an opening in the reservoir such that fluid is able to flow over the filter membrane; a base to receive the filtrate after it passes through the membrane, the base including a path through which the filtrate is guided to an outlet from the filtration cell; a piercing instrument supported in the filtration cell adapted to pierce a container holding the fluid to be filtered, the piercing instrument including a hollow interior in open communication with the reservoir and adapted to be in open communication with an interior of a pierced fluid container, and a flow channel extending between the piercing instrument and the reservoir such that the hollow interior of the piercing instrument is in communication with the reservoir through the flow channel, wherein the flow channel is open to the filter membrane so that fluid to be filtered can be directly passed from a fluid container over the filter membrane as it is transferred from the hollow interior of the piercing instrument, through the flow channel and into the reservoir.

A process for directly transferring a specimen of a fluid to be filtered from a fluid container to a filtration cell is included within the invention and comprises (a) providing a filtration cell comprising a reservoir, a filter membrane operatively associated with an opening in the reservoir, a base configured to receive filtrate passing through the membrane, the base including a path through which the filtrate is guided to an outlet from the filtration cell, a piercing instrument adapted to pierce a container holding the fluid to be filtered, the piercing instrument including a hollow interior in fluid communication with both the reservoir and an interior of a pierced container, and a flow channel extending between the piercing instrument and the reservoir, the flow channel being open to the filter membrane; (b) providing a container holding a quantity of fluid to be filtered; (c) piercing the container with the piercing instrument; (d) providing an airtight connection between the reservoir and a source of air; (e) alternately pressurizing the reservoir with air, and then releasing the air pressure from the filtration cell such that the fluid reciprocally flows across the filter membrane; and (f) collecting the filtrate from the membrane.

In one preferred embodiment of the process, the filtration cell further comprises a second reservoir in fluid communication with the flow channel between the reservoir and the piercing instrument, step (d) further comprises providing an airtight connection between the second reservoir and the source of air, and step (e) further comprises alternately (i) blocking the flow of air into the reservoir, pressurizing the second reservoir with air, and venting the reservoir to release the air pressure and (ii) blocking the flow of air to the second reservoir, pressurizing the reservoir with air, and venting the second reservoir such that the fluid to be filtered flows initially from the initially from the container to the reservoir then reciprocally from the reservoir to the second reservoir across the filter membrane.

In a further preferred embodiment of the process, the filtration cell further comprises an air inlet port having a passageway therethrough and adapted to receive air from a pressure source, and the method further comprises pressurizing the container after fluid to be filtered is initially transferred to the reservoir to ensure that a substantial amount of the fluid flows from the container to the reservoir.

The invention also includes a filtration cell capable of direct sampling of a fluid from a container. The filtration cell comprises (a) a first reservoir and a second reservoir to receive the fluid to be filtered; (b) a filter membrane capable of filtering the fluid to provide a filtrate, the membrane being operatively associated with an opening in the first reservoir and an opening in the second reservoir such that fluid is able to flow over the filter membrane; (c) a base to receive the filtrate after it passes through the membrane, the base including a path through which the filtrate is guided to an outlet from the filtration cell; (d) a piercing instrument supported in the filtration cell adapted to pierce a container holding the fluid to be filtered, the piercing instrument including a hollow interior in open communication with the first reservoir and the second reservoir and adapted to be in open communication with an interior of a pierced fluid container; and (e) a flow channel extending between the piercing instrument and the second reservoir and in fluid communication with the first and second reservoirs such that the hollow interior of the piercing instrument is in communication with the first and second reservoirs through the flow channel, wherein the flow channel is open to the filer membrane so that fluid to be filtered can be directly passed from a fluid container over the filter membrane as it is transferred from the hollow interior of the piercing instrument through the flow channel and into the first reservoir and thereafter flow reciprocally from the first reservoir to the second reservoir.

The invention also includes a filtration system capable of direct sampling of a fluid from a container. The filtration system comprises a filtration cell and a filter head in communication with a pressure source and adapted to seal the reservoir of the filtration cell. The filtration cell of the filtration system comprises a reservoir to receive the fluid to be filtered; a filter membrane capable of filtering the fluid to provide a filtrate, the membrane being operatively associated with an opening in the reservoir, a base to receive the filtrate after it passes through the membrane, the base including a path through which filtrate is guided to an outlet from the filtration cell; a piercing instrument supported in the filtration cell adapted to pierce a container holding the fluid to be filtered, the piercing instrument including a hollow interior in open communication with the reservoir and adapted to be in open communication with an interior of a pierced fluid container, and a flow channel extending between the piecing instrument and the reservoir such that the hollow interior of the piercing instrument is in communication with the reservoir through the flow channel, wherein the flow channel is open to the filter membrane so that fluid to be filtered can be directly passed from a fluid container over the filter membrane as it is transferred from the hollow interior of the piercing instrument, through the flow channel and into the reservoir.

BRIEF DESCRIPTION OF THE SEVERAL VIEW OF THE DRAWINGS

The foregoing summary, as well as the following detailed description of the invention, will be better understood when read in conjunction with the appended drawings. For the purpose of illustrating the invention, there is shown in the drawings, where like numerals indicate like elements throughout, an embodiment which is presently preferred. It should be understood, however, that the present invention is not limited to the particular arrangement and instrumentality shown.

DETAILED DESCRIPTION OF THE INVENTION

Figure 1:
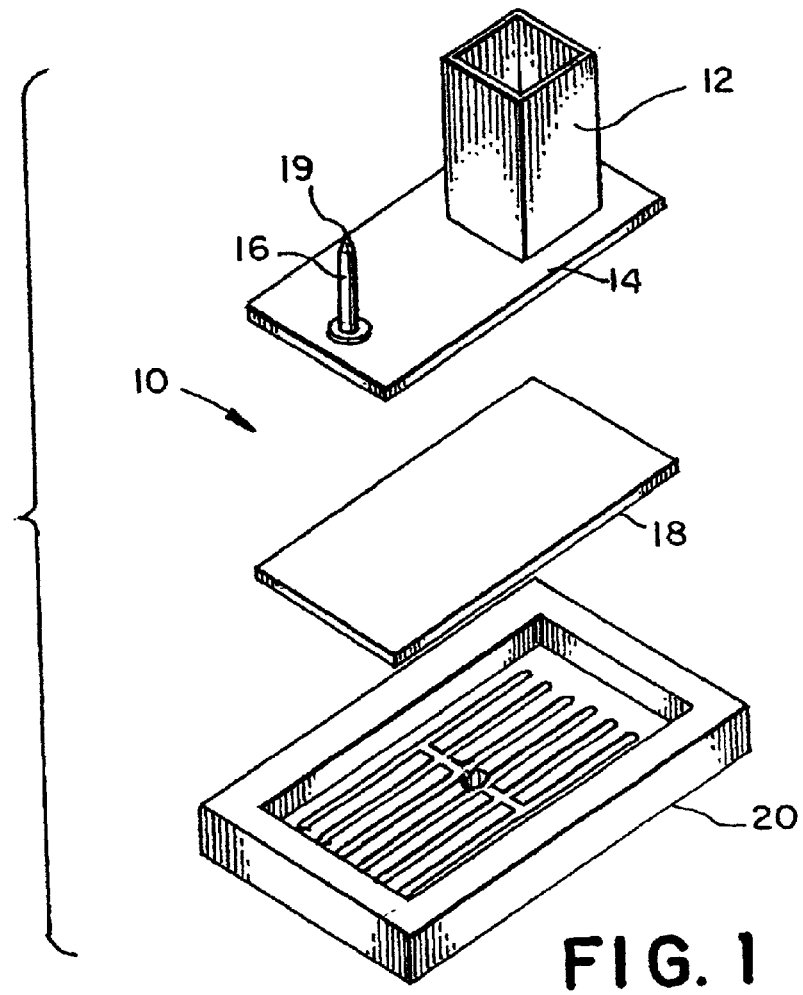
FIG. 1 is an exploded perspective view showing the components of the microfiltration cell in accordance with the present invention.
Figure 2:
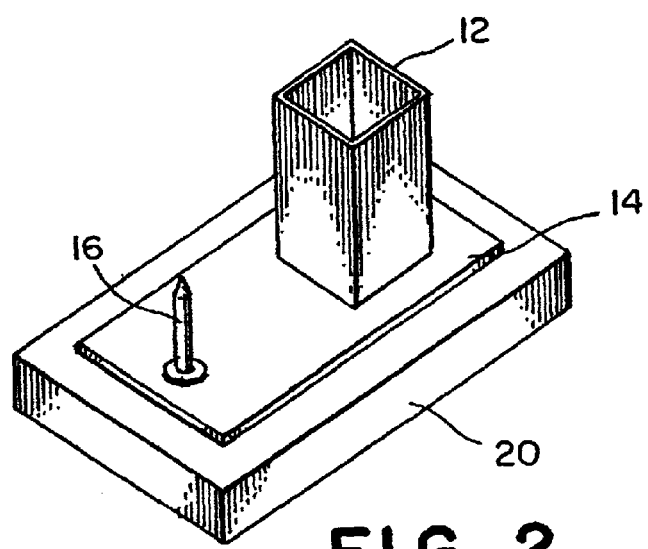
FIG. 2 is a perspective view of the assembled microfiltration cell.

Certain terminology is used herein for convenience only and is not be taken as a limitation on the present invention.

The words "right," "left," "outwardly" and "inwardly", and "down" and "up", designate directions in the drawings to which reference is made. The words "proximal" and "distal" refer to directions away from and closer to, respectively, the interior of the filtration cell according to the present invention. The terminology includes the words above specifically mentioned, derivatives thereof, and words of similar import.

Figure 3A:
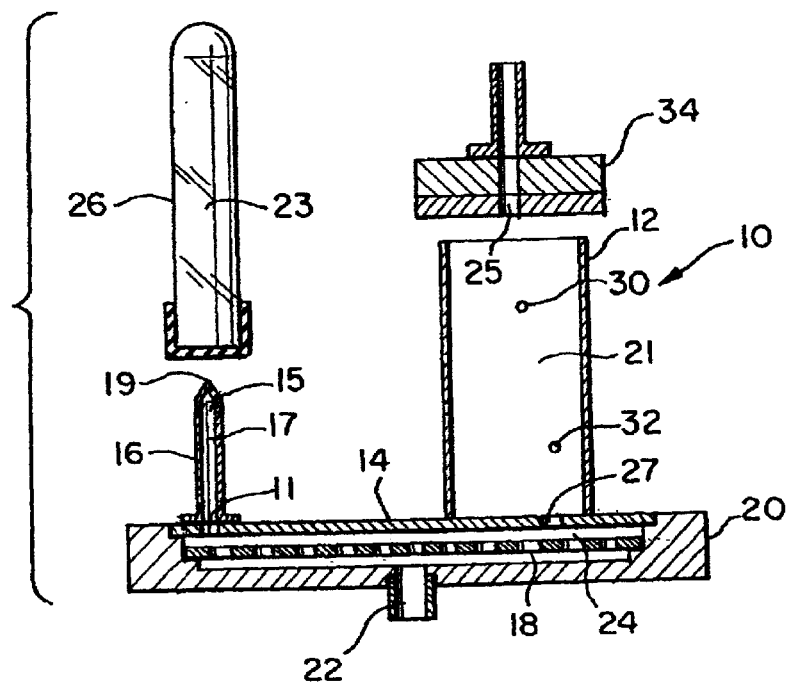
FIG. 3A is a schematic illustration of the direct specimen microfiltration system according to the invention for small volume microfiltration.
Figure 3B:
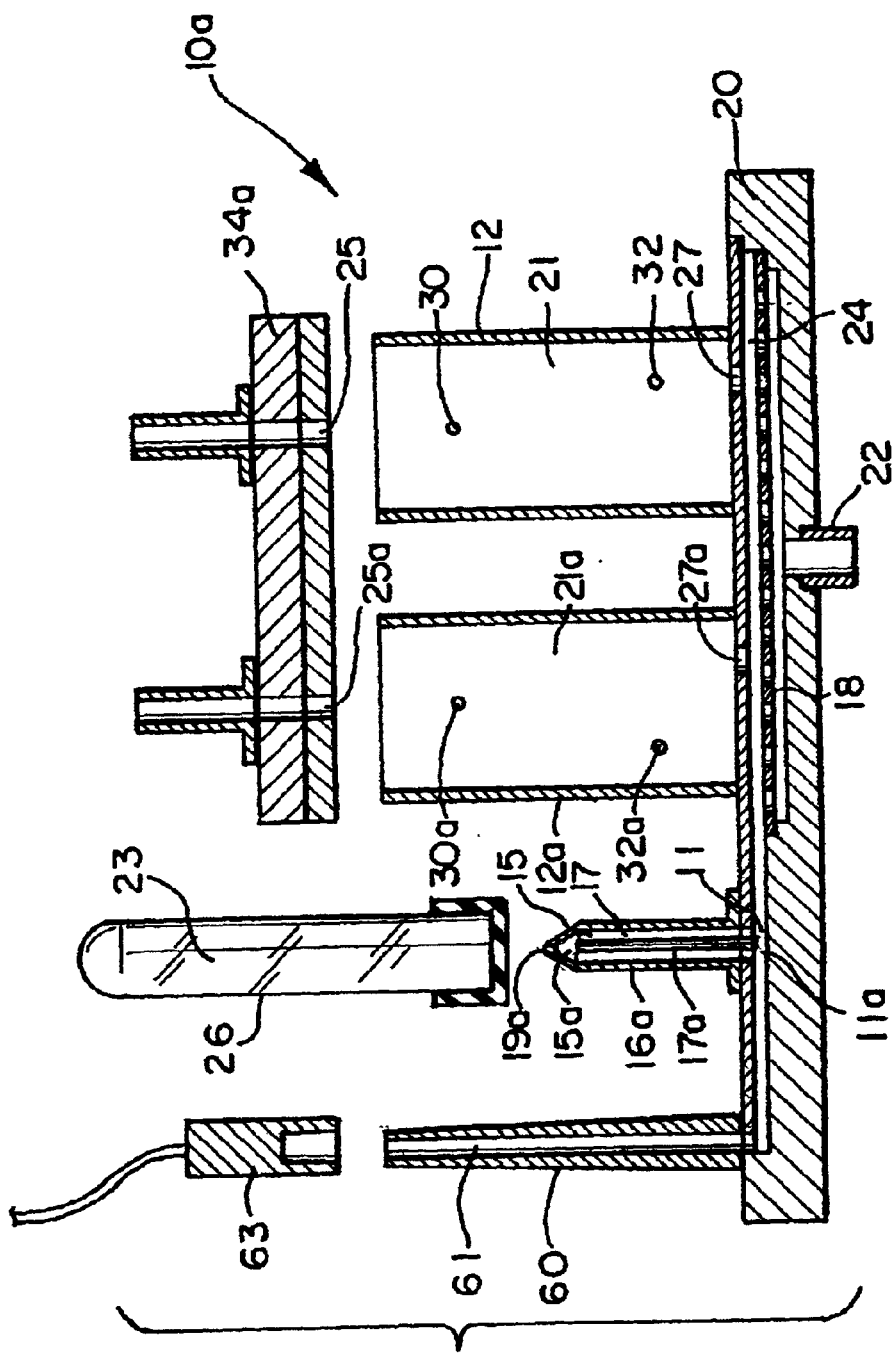
FIG. 3B is a schematic illustration of a direct specimen microfiltration system according the invention for large volume microfiltration using an air inlet port.
Figure 3C:
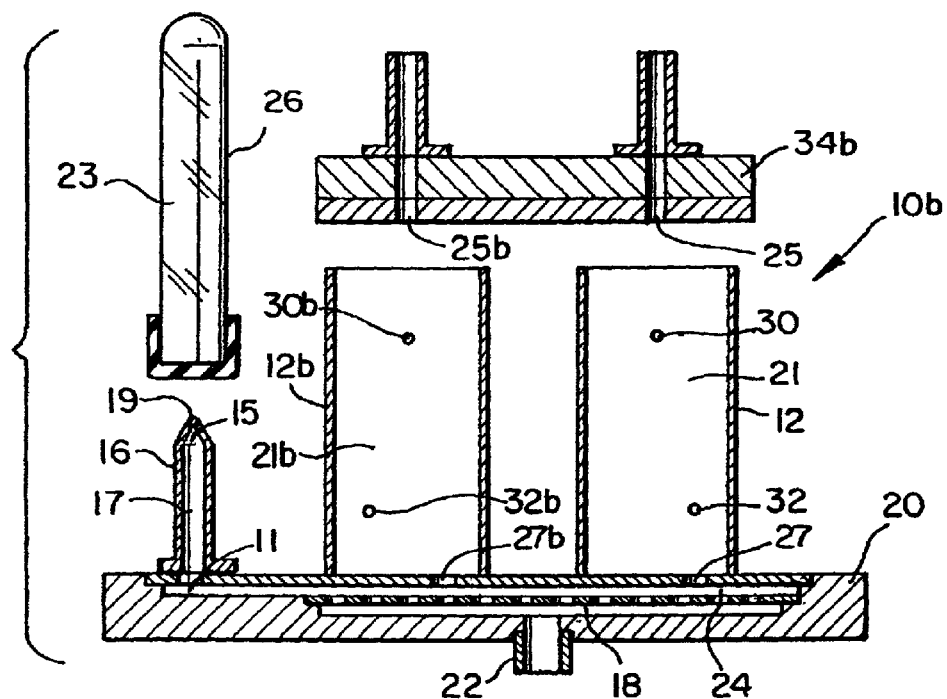
FIG. 3C is a schematic illustration of a direct specimen microfiltration system according to the invention for large volume microfiltration.

The following describes preferred embodiments of the invention. However, it should be understood, based on this disclosure, that the invention is not limited by the preferred embodiments described herein. Referring now to the drawings in detail, there is shown in FIGS. 1, 2, 3A, 4A–4C and 5, a preferred embodiment of a filtration system, filtration cell for direct sampling of a fluid from a container and a process for directly transferring a specimen of a fluid to be filtered from a fluid container to a filtration cell. FIGS. 3B and 3C represent additional features which may be provided to the preferred embodiment of FIG. 3A in order to handle larger volumes of fluid to be filtered. Further, FIGS. 6 and 7 demonstrate a further variation of the preferred embodiment which includes a preferred bottom fillable sample collection well.

As used herein, "filtration" is preferably intended to mean passing a fluid to be filtered through a filter membrane to result in collected filtrate for use in sample analysis and encompasses both smaller and larger volume specimens preferably using microfiltration. Microfiltration is intended to mean filtration of a specimen to separate particles of from about 0.01 $\mu$n to about 20 $\mu$n in size as measured in the longest dimension of the particle. A microfiltration evaluation module is intended to refer to a computer driven microfiltration device for scientific evaluation of a microfiltration process. A microfiltration system encompasses a microfiltration unit, which according to the present invention is a fully enclosed, fully functional specimen processing unit which is preferably self-contained, a compromised specimen tube piercing feature and other related features as described herein. A microfiltration cell, for a 0.5 ml cell, and preferably of configuration as shown in FIG. 3A, is preferably of a size, for example, of from about 1" high with respect to the piercing instrument height as described herein, and about 1½" in width and about ¾" in length across the base area as described herein. The reservoir should be about 16/32" in width and height and about 8/32" length across the opening at the top of the reservoir. That is, the top opening of the reservoir should measure about 16/32"×8/32", and need not be square or rectangular in overall cross sectional shape. The embodiment of FIG. 3A as described further herein is preferably about 0.5 ml in volume. With respect to the two reservoir embodiments shown in FIGS. 3B and 3C, as described elsewhere herein, the cells are preferably taller to accommodate larger volumes, and are preferably about 20/32"×20/32" across the opening at the top of each of the reservoirs and about 1/¼" in height with respect to each reservoir. The larger volume cells may also have a base of about ¾"×2 ¾". The piercing instrument is preferably about ¾" to about 1" in height and the sample outlet may be about 8/32" in length. These size parameters are intended to indicate the most preferred embodiment sizes, but should not be considered limiting as the cells may be varied in size to accommodate different applications and cell configurations in accordance with the description herein.

A direct specimen transfer filtration cell according to the present invention is a microfiltration cell that removes the specimen from a specimen tube and provides a sample for analysis directly. A sample taken from the cell may be collected by several methods, including use of a spout bottom in which the outlet of the microfiltration cell can dispense filtrate directly into another container, and the use of a bottom fill well in which the filtrate is collected in a well on the microfiltration cell. In one embodiment of the invention the well is fed with filtrate from the bottom Also as used herein with reference specifically to the present invention, small volume microfiltration direct specimen transfer filtration cells include those which have one reservoir chamber and which can produce approximately or precisely 100 $\mu$l of filtrate and large volume microfiltration direct specimen transfer filtration cells include cells according to this invention which has at least two reservoir chambers and is capable of processing approximately or precisely 1.5 ml of filtrate.

The term "specimen" is intended to refer to a fluid to be tested, such as a blood specimen taken from a patient. A "sample" is intended to refer to filtrate resulting from processing in a microfiltration cell such as plasma or serum taken from a blood specimen. The filtrate and fluid to be filtered in the specimen and sample, respectively, however, should not be considered limited to blood and blood components. Further, while the above terms have the preferred meanings as described above, they are further defined within the context and meaning of the disclosure and their use should not be deemed limited by the preferred definitions set forth above.

The present invention eliminates the specimen transfer operation of prior art filtration systems and thus enhances the operation of the overall system. In one embodiment, the liquid container becomes one chamber of the filtration cell which heretofore has used two filtration chambers or "reservoirs," each chamber being alternately filled and emptied as the fluid is passed over the microfiltration membrane as described in U.S. Pat. No. 5,000,923. This is an acceptable, simple design which and works well for small volumes.

The present invention will now be described with respect to the following non-limiting description and with reference to the drawings. The new filtration cell of the present invention which is capable of direct sampling of a fluid specimen from a container, herein generally referred to as 10 and as shown in exploded schematic view in FIG. 1, comprises a reservoir 12 to receive the fluid to be filtered, a filter membrane 18 capable of filtering the fluid to be filtered to provide a filtrate for analysis, a base 20 to receive the filtrate after it passes through the membrane 18 and a piercing instrument 16 which is supported in the filtration cell and adapted to pierce a container holding fluid to be filtered. In addition, the filtration cell includes a flow channel 24 which extends between the piercing instrument 16 and the reservoir 12.

The single reservoir chamber serves the same purpose and made be configured in the manner of one of the reservoirs 108 in U.S. Pat. No. 5,000,923, incorporated herein by reference. References to components and features shown in U.S. Pat. No. 5,000,923 will use the reference numbers of that patent for convenience. The reservoir 12 as shown in FIG. 1 herein is mounted on a support 14 which defines a flow channel 24 (shown in FIG. 3A) whose purpose is like the flow channel 127 in U.S. Pat. No. 5,000,923; that is, to provide a channel through which the fluid to be filtered can flow back and forth over the surface of the membrane 18 tangentially for achieving microfiltration of the specimen to form a filtrate for use as a sample for analysis.

Mounted on the support 14 as shown in FIG. 1 schematically and in FIG. 3A is a hollow piercing instrument 16 which has a hollow interior 17 in preferably open, fluid communication with the flow channel, and also open at or near its piercing end 19. The hollow interior 17 is also in fluid communication with the interior space 21 of the reservoir 12 through the flow channel 24 and is adapted to be in preferably open, fluid communication with the interior area 23 of a container 26 for dispensing a specimen to be filtered and analyzed once the container 26 has been pierced by the piercing end 19. The sharp pointed projection or end 19 of the piercing instrument is adapted to pierce a container for the fluid to be filtered and which has a first opening 15 therethrough and a second opening 11 which is in fluid communication with the reservoir through the flow channel at the bottom of the piercing instrument.

The flow channel 24 which extends between the piercing instrument and the reservoir is open to the filter membrane 18 so that fluid to be filtered can be directly passed from a fluid container 26 over the filter membrane 18 as it is transferred from the hollow interior 17 of the piercing instrument 16, through the flow channel 24 into the reservoir 12.

Figure 4C:
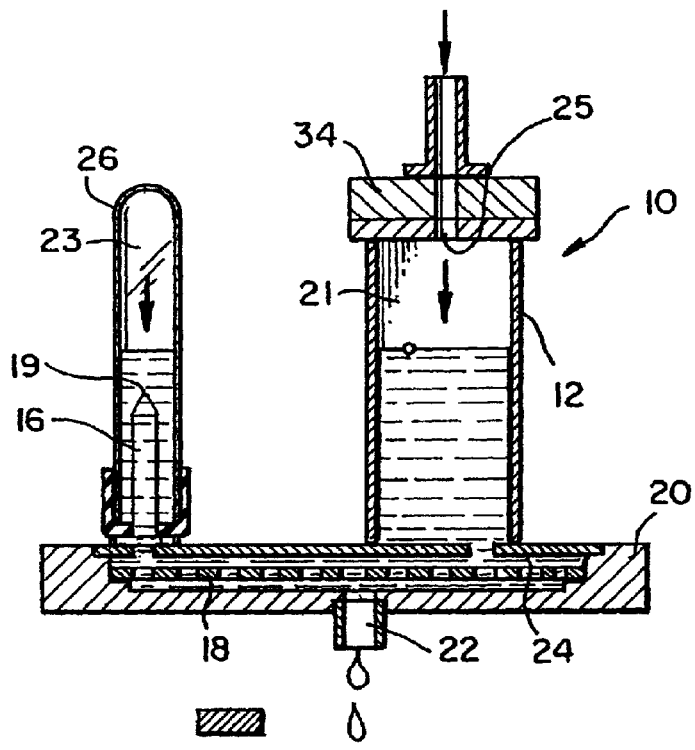
FIGS. 4A, 4B and 4C represent a schematic illustration of the process for direct sampling for microfiltration using a direct sampling device according to the present invention.
Figure 4A:
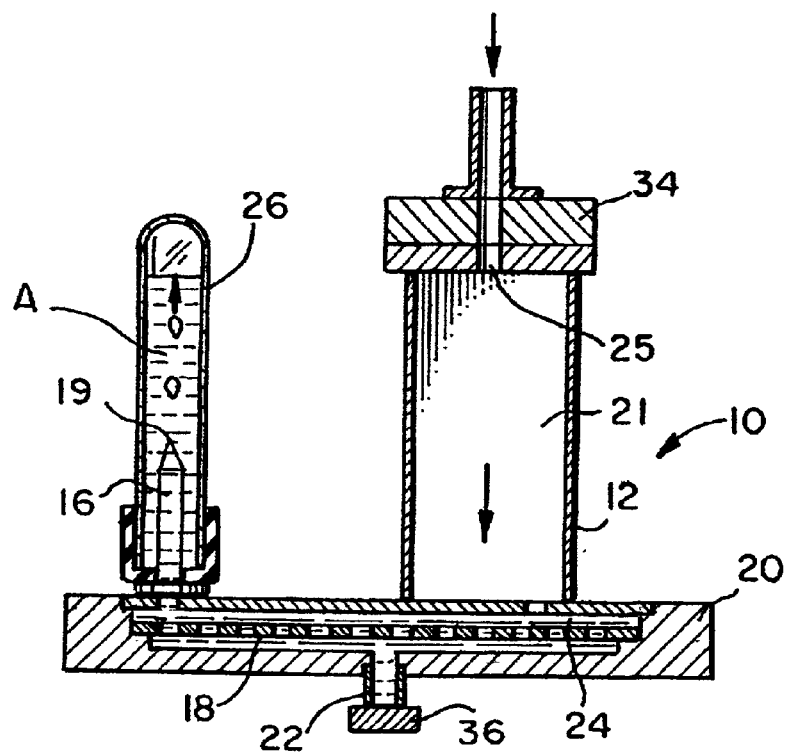

The filtration cell 10 as described can be used to directly filter the fluid in the container. As such, the present invention further provides a process for directly transferring a fluid to be filtered from a fluid container, such as container 26 to a filtration cell. The process will be described generally with reference to FIGS. 4A–4C. A filtration cell is first provided for use in such a method and preferably includes providing the filtration cell 10 or other embodiments of the filtration cell as described further herein. Then a container 26 is provided which holds a quantity of fluid A to be filtered and is placed on the piercing instrument such that pointed projection 19 compromises the container and the piercing instrument penetrates the container as shown in FIG. 4A. This assembly is then moved to a filtration station that includes a connecting filter head such as filter head 34 shown in FIG. 3A and is preferably operatively attached to an air supply. The connecting filter head clamps down on the top of the reservoir chanter creating an airtight connection between the reservoir and the source of air thereby sealing the filter head against the reservoir. While reference is made throughout to air as a pressurizing gas, it should be understood that other, preferably inert gases such as nitrogen, argon and the like should be considered within the scope of a pressurizing gas and will be referred to collectively herein as "air" or a "pressurizing gas" or the like for convenience only.

Figure 4B:
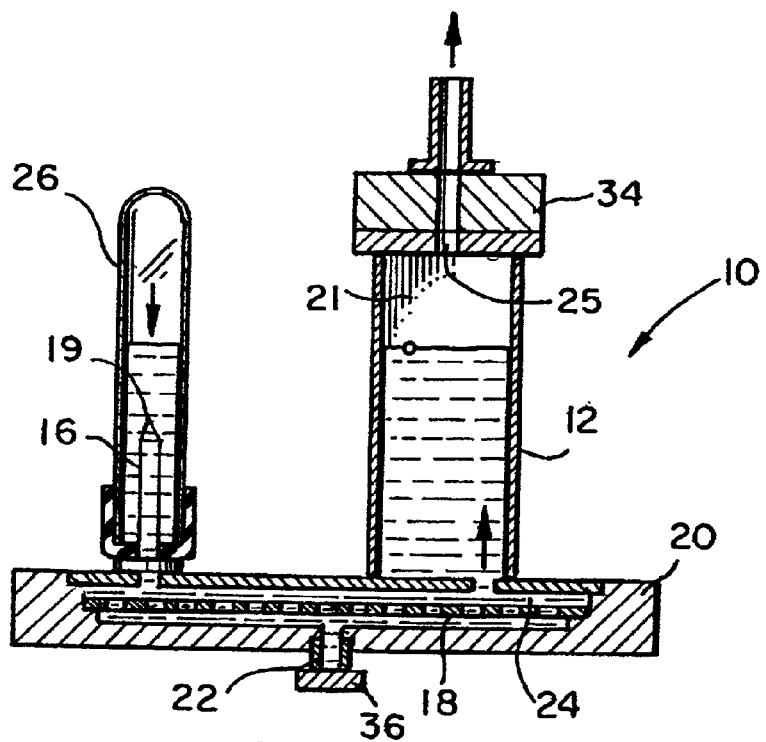

The outlet port 25 in the base of the filter is also sealed to provide an airtight system A volume of air is pumped into the reservoir chamber, through the flow channel, and into the specimen tube 26 to pressurize the tube and filtration cell 10 as shown in FIG. 4A. Thereafter, the air pressure is vented as shown in FIG. 4B. The process then provides for alternately pressurizing the reservoir with air, and then releasing or venting the air pressure from the filtration cell 10 such that the fluid flows reciprocally across the filter membrane 18 as shown in FIG. 4C. After leaving the filtration cell through outlet 22, the filtrate is then collected as described further below.

The process further includes withdrawing the piercing instrument, preferably by automated process system equipment as described further below. However, the piercing instrument may be manually withdrawn as well. The process may also be practiced using the further preferred embodiments of a filtration cell according to the invention as shown in FIG. 3B or 3C.

The preferred embedment of a filtration cell 10b shown in FIG. 3C, has a second reservoir 12b and a filter head 34b which has a corresponding second opening 25b for the second reservoir 12b. The second reservoir 12b can receive fluid to be filtered and may be configured in the manner of the first reservoir 12 of FIG. 3A, and the reservoirs 12, 12b are preferably substantially identical, and most preferably identical. The filter membrane 18 in FIG. 3C is preferably operatively associated with the opening 27 in the first reservoir 12 to the flow channel 24 as in the filtration cell of FIG. 3A and also operatively associated with the opening 27b in the second reservoir 12b in FIG. 3C. The flow channel 24 in FIG. 3C extends between the piercing instrument 16 which is preferably the same as the instrument 16 in FIG. 3A and the first reservoir 12 and is in fluid communication with both the first and second reservoirs 12, 12b such that the hollow interior 17 of the piercing instrument is in communication with both reservoirs through the flow channel which is also open to the filter membrane 18. The fluid to be filtered passes directly from the container 26 over the membrane and is transferred from the hollow interior of the piercing instrument, through the flow channel and into the first reservoir 12 and thereafter, the fluid passes reciprocally from the first reservoir to the second reservoir for handling larger volumes of specimen to provide larger samples for analysis using the control over sample size provided by the present invention.

The process using the embodiment of FIG. 3C includes the steps as described above and further providing an airtight seal between the second reservoir 12b and the source of air, which is preferably the same source of air feeding reservoir 12. The flow of air into the first reservoir 12 is first blocked using a valve, gate, or any other similar apparatus to controllably seal the outlet 25 into the reservoir from the filter head. The second reservoir 12b is then pressurized with air, followed by venting of the first reservoir 12 to cause fluid in the specimen tube 26 to pass into the first reservoir through the hollow interior of the piercing instrument, the flow channel and opening 27 into the interior 21 of the reservoir 12. The second reservoir 12b is then blocked by use of a valve or other similar apparatus as noted above and the first reservoir 12 pressurized with air. The second reservoir is then vented causing fluid in the first reservoir to flow through opening 27 and flow channel 24 into opening 27b and space 21b in the second reservoir 12b while passing tangentially over the membrane 18. These steps of blocking, pressurizing and venting the alternating reservoirs are then repeated and reciprocal flow occurs between the first and second reservoirs occurs across the membrane, which is preferably a mircoporous membrane to filter, and preferably microfilter a specimen to provide a filtrate for analysis. As can be seen from the above, the filtration cell 10b of FIG. 3C operates in the same manner as the filtration cell 10 of FIG. 3A except reciprocal flow occurs between the two reservoirs instead of between the interior of the specimen tube and the reservoir 12 allowing for processing of larger volumes. Further, a multiport filter head with communication through two outlets 25 to the pressure source is used to seal both reservoirs and alternatively vent and pressurize the reservoirs.

Alternatively, the process of the invention may be carried out using the filtration cell 10a shown in FIG. 3B. FIG. 3B shows a filtration cell which is also a two reservoir embodiment having a first reservoir 12 and second reservoir 12a, a filter head 34a having two outlets for 25, 25a for pressurizing the respective reservoirs and a modified piercing instrument 16a as well as an air inlet 60. The reservoir 12a is in fluid communication with the first reservoir 12 through opening 27a and flow channel 24 and with the interior hollow space 17 of the piercing instrument 16a which has pointed projection 19a. The piercing instrument has a first hollow interior space 17 having an open end 15 in communication with the interior 23 of the specimen tube 26 and a bottom opening 11 in communication with flow channel 24. The piercing instrument further includes a second hollow interior space 17a which has an opening 15a also in communication with the interior 23 of the specimen tube 26 and a second bottom opening 11a which passes through filtration cell support 20 to the longitudinally extending passageway 61 of an air inlet port 60 such that the air inlet port 60 is in fluid communication with the hollow interior 17a of the piercing instrument 16a The air inlet 60 is adapted to receive a pressurizing port such as port 63 shown schematically in FIG. 3B. The port 63 may be any suitable pressure source, preferably inert which is adapted to attach to the inlet 60 in a substantially airtight manner to pressurize the interior 23 of the specimen tube 26, preferably when the specimen is initially transferred from the tube 26 to ensure that an ample amount of the fluid from the container or specimen tube 26 is transferred to the reservoir 12, which amount depends upon the desired amount of sample to be derived from the specimen. The pressure source for connecting through pressuring port 63 may be a separate pressure source, but is preferably the same pressure source used to pressurize the reservoirs 12, 12a through filter head 34a The filtration cell 10a and process using that cell, as with the cell 10b, may process larger volumes of fluid to be filtered to provide larger volumes of filtrate for sampling and analyzing if desired.

The filtration cell incorporates the unique ability to reciprocally or tangentially flow the specimen across a membrane with only a single pressure input as shown in FIG. 3A. The residual pressure in the fluid container causes a portion of the specimen to flow through the piercing instrument, through the flow channel and into the reservoir chamber. But this time the seal on the outlet port may be removed. Air is once again pumped into the reservoir chamber causing the specimen to flow through the flow channel and back into the specimen tube. Consequently, the fluid passes back and forth over the filter membrane. Filtrate is collected in the base of the filtration cell and dispensed through the outlet port. The foregoing cycle is repeated until a desired quantity of filtrate is collected. The filtrate can be dispensed as collected, dispensed as an approximate volume, or precisely measured. As a result, the invention provides the ability to control the manner in which samples are collected for various applications and uses of the microfiltration cell and with differing degrees of control over the samples. If the fluid is anticoagulated whole blood, the filtrate is plasma.

The foregoing process, using the filtration cells 10, 10a, 10b shown in FIGS. 3A–3C and using those cells in a filtration system incorporating such filtration cells in combination with one or more of a filter head 34, 34a, 34b and, if appropriate, an air inlet port 60 and/or a pressurizing port 63, has proven to substantially reduce the 45 seconds presently required to transfer a specimen from a container to a reservoir for microfiltration. Early testing indicates that the time to pick a container, place it on the filtration cell, and move the cell into position for filtration takes about 10 seconds.

The present invention, in the embodiments described herein, provide alternative configurations for introducing air pressure into the specimen tube to full remove the blood and enable the user to handle larger volumes. If only a single reservoir is used, the ability to separate contents of 5 ml or larger becomes more difficult. As a result, for larger specimens, the two reservoir design, described herein, is useful and reduces damage which may be caused to liquids to be purified, such as blood, which may be damaged by the repeating cycling through the small orifice in the prior design and due to the concentration of cells after 150 $\mu$l of plasma has been removed from the blood specimen The embodiments described herein provide an optimal small volume flow channel for smaller specimens and for larger volumes, an extra cell and/or a side air inlet, such as air inlet 60, including varying pressurization schemes may be used to assist in forcing substantially all, preferably all fluid from the specimen tube as described further below for handling larger volumes.

Further, the direct specimen transfer filtration cells of the present invention in the preferred embodiment is physically joined to the sample well or container through an outlet. As such, the integrity of the sample identification is maintained throughout the filtration process and subsequent processes, which prevents significant errors which may cause patient harm or death as a result of a mislabeled or mishandled sample or because of aliquot errors. In addition, possible sample contamination from handling is avoided.

Another benefit of a system that operates without sample or specimen transfer is that it is a closed system which is fully enclosed and automated As such, it is safer to operate since there is no exposure to hazardous samples or specimens, rinse and waste fluids as would occur during the now eliminated transfer step. Moreover, there is no carry-over of excess fluid as ordinarily occurs during a transfer process. Specimens and samples, particularly biologicals, undergo artifactual changes caused by pH and other changes resulting from atmospheric exposure. A closed system precludes such changes and maintains the specimen and sample in a more physiologic environment throughout the process of microfiltration and sample handling. Consequently, there is less risk of contamination or dilution even in the micro-volume range that the system capabilities can handle, and the system works at lower volumes.

Yet another advantage of the present invention is that it allows the user to do analyses that could not previously be done. Elimination of mechanical separation processes (such as centrifugation) results in better filtrates capable of responding to the analytic techniques which heretofore have been precluded from use. Other separation technologies, including centrifugation, vertical filtration, chemical and the like result in either contaminated filtrates or filtrates in which the analytes are affected by the process such that, typically, larger specimens must be processed. Crossflow microfiltration produces "clean filtrates." Further, microfiltration is not constrained by sample size. Analytical techniques applied to microfiltered samples are not hindered by the presence of unwanted particulates nor does process affect the analytes. Accordingly, very small sample volumes can be processed for analysis. The ability to process and manage microvolumes of samples is particularly useful in many applications requiring a high degree of purity and unaffected analyte, such as, for example, in veterinary applications where plasma rather than serum is the preferred analytical matrix.

The generation and control of filtrates may be done in parallel with the filtration cycle. The present invention provides the benefit of being able to dispense filtrate in various ways for exercising control over the manner in which the filtrate is collected and dispensed, for example, the filtrate may be taken in an unmeasured collection, as an approximate measure, as a precise measure even in microliters.

Figure 6:
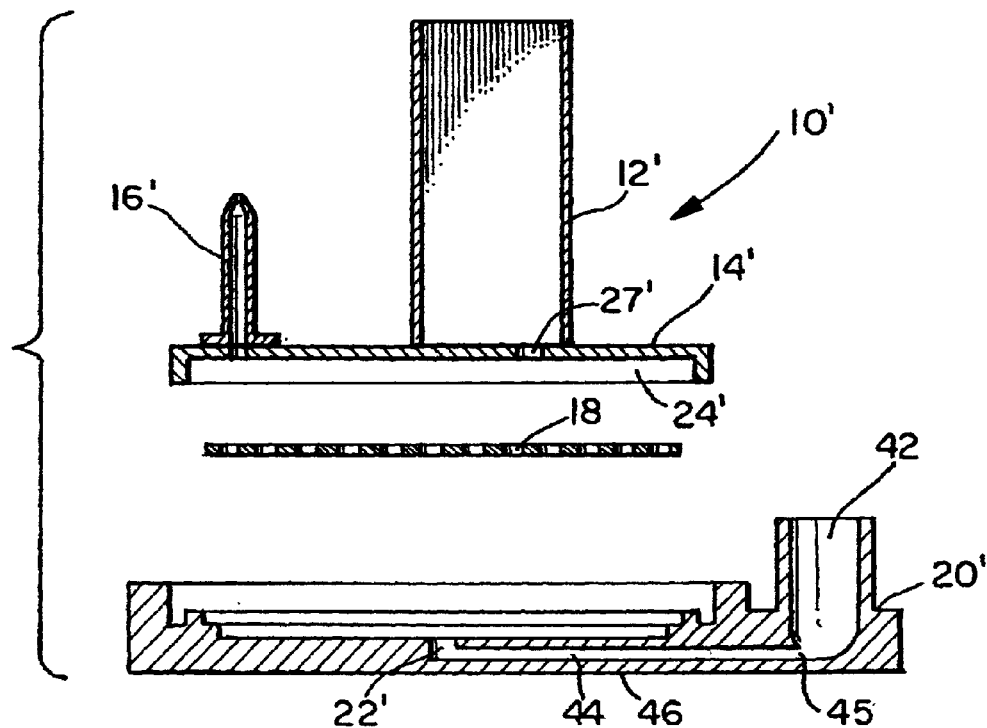
FIG. 6 is an exploded view showing a microfiltration cell with a bottom fill well.
Figure 7:
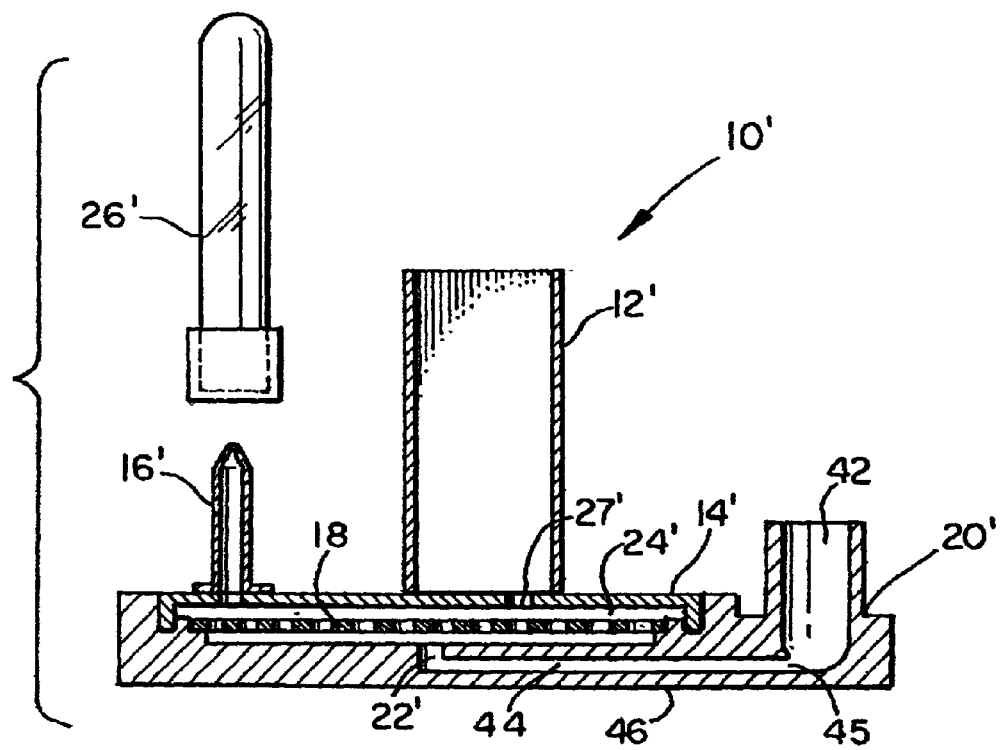
FIG. 7 shows an assembled microfiltration cell with a bottom up fill well.

In another embodiment of the present invention, as best shown in FIGS. 6 and 7, the filtration cell is configured so that no air is trapped under the filtrate. One of the primary applications, although, not the exclusive application, since the invention has many possible uses, of the present invention is to improve the process for separating plasma from whole blood by microfiltration. One approach is to allow the plasma to flow into the top of an open well. Depending upon how the plasma drops fill the well, there is a possibility that air can be trapped under the plasma because it is relatively viscous. Trapped air is a problem especially when working with small volumes such as in the micro liter range. This in turn presents problems for automated analyzers, particularly instruments that transfer a measured portion of the plasma to a test cuvette by aspiration. The instrument cannot sense aspirated air. Microfilter samples exposed to air may be affected by pH and other changes that could affect analytical results, as well as introducing a risk of sample contamination when handled in the traditional manner. Consequently the volume dispensed is inaccurate.

The present invention overcomes the problem of trapped air in an open well by providing a microfiltration cell 10' that fills a well from the bottom up. Consequently, the plasma remains uniform as it fills the well. Another benefit of providing a well that fills from the bottom up is that the microfiltration cell itself requires less expensive parts and is easier to assemble, thereby reducing its overall cost to manufacture.

In further discussion of the preferred embodiments of the filtration cells of the invention, and referring now to the drawings, FIG. 1 shows an exploded view of a filtration cell for direct sampling of fluid from a container. The filtration cell 10 includes the open top reservoir 12, as described above, mounted on a support 14. The reservoir 12, as shown in FIG. 3A, is open at the bottom at opening 27.

The support 14 also retains an upstanding piercing instrument 16. The piercing instrument 16 is hollow having interior space 17 and opens through the support 14 as shown in FIG. 3. The piercing instrument is also open to its hollow interior at or adjacent to its sharpened end 19. The purpose of the piercing instrument is to pierce the container 26 holding the fluid to be filtered as hereinafter described.

The filtration cell includes a filter membrane 18 whose purpose is to filter fluid passing across its top surface. Filter membrane 18 can be a microporous membrane but the invention is not limited to any particular type of filter. Filtrate moves through the filter membrane 18 and is collected in the base 20. The base 20 collects the filtrate and guides it via channels to an outlet port 22. The guide path for the filtrate is substantially the same as is disclosed in U.S. Pat. No. 5,000,923 which is referred to and incorporated herein by reference.

As best shown in FIG. 3A, the piercing instrument 16 and reservoir 12 are in open communication with each other through a flow channel 24. Flow channel 24 is above the membrane 18. The fluid to be filtered passes through this flow channel from a specimen container 26 to the reservoir 12. As described herein, the fluid also reverses its path and moves from the reservoir through the flow channel to the specimen container. This reciprocal flow results in filtration of the fluid by the microporous membrane 18. The filtrate is collected and passes through outlet port 22.

The specimen container 26 may be any conventional container for holding a specimen of fluid to be analyzed. As illustrated, the specimen container 26 is a specimen tube closed at its open end by a conventional closure device having a relatively soft material, such as a polymeric or elastomeric material that can be penetrated by the piercing instrument 16. However, it is within the scope of the invention to use a container which is itself capable of being breached by a piercing instrument and the invention should not be considered limited with respect to the particular type of container to be used, except to the extent it may be compromised by a piercing instrument such as piercing instrument 16. The closure device 28 ray also include a septum or similar device.

In the preferred embodiment, the reservoir 12 is provided with upper and lower optical paths 30 and 32, respectively. In the further preferred, alternative embodiments of FIGS. 3B and 3C, optical paths 30a, 30b, 32a, 32b are further provided to the second reservoirs 12a, 12b, respectively and are otherwise the same as optical paths 30, 32 described herein. The optical paths 30 and 32 may each take the form of a light conductor built into the wall of the reservoir, or the reservoir may simply be made of a transparent material. The purpose of light conducting paths 30 and 32 is to permit detection of the level of fluid in reservoir 12 and/or reservoirs 12a, 12b. When light path 30 is blocked, a sense signal indicates that the reservoir is filled to its desired level. When light path 32 is unblocked, a sense signal indicates a low level of fluid in reservoir 32. Sensing this high level and low level of fluid in paths 30 and 32 is used to control the reciprocal flow of fluid in and out of the reservoir, and hence the back and forth flow of the fluid over the filter membrane 18. The low level detector stops the flow of the specimen, preventing air from entering the flow channel which avoids introduction of air into the specimen and sample which could result in foaming in the specimen and/or sample. Similarly, an optical path can be provided in the well or other collection receptacle to be used with a system for detecting when the well has been filled by the filtrate to a desired level.

The process for direct sample filtration is best understood by reference to FIGS. 4A, 4B and 4C as noted above. As illustrated, a specimen container 26 is placed on the piercing instrument 16 which pierces through the closure 28. The air connector 34 clamps down on the top of the reservoir 12 thereby creating an airtight seal. Simultaneously, the outlet port 22 is closed, preferably using a removable closure device such as closure cap 36 in FIG. 4A. See U.S. Pat. No. 4,695,430 for a more detailed description of the air connector which is otherwise referred to herein as filter head 34, such disclosure in U.S. Pat. No. 4,695,430 being incorporated herein by reference. The outlet port sealing mechanism can be simply a sealing mechanism that is reciprocally moved into airtight closing relation with the outlet port 22. The cell 10 is now sealed and airtight.

The next step in the process is to apply pressurized air through the filter head 34. The air passes through the flow channel 24, the piercing inset 16 into the container 26. Air is preferably applied at a pressure of approximately 2 to 10 pounds per square inch (psi). The air pressure should be kept as low as possible consistent with obtaining proper filtration. Low air pressure avoids potential physical damage to, such as cellular deformity, and the migration of constituents of the specimen being filtered, particularly with respect to biological fluids. For example, it is desirable to use a pressure of 2.75 psi (120 mm of mercury) when processing blood because this is equal to normal blood pressure in the human body.

Next, the air pressure is relieved and air exhausted from the reservoir 12. The residual air pressure in the container 26 forces the specimen of blood to flow through the piercing instrument, through the flow channel and into the reservoir 12. Flow in the direction described continues until the upper optical path 30 senses the specimen or fluid level. Then pressurized air is again applied to the surface of the fluid within the reservoir 12. This time the outlet port 22 is opened by removing the seal 36. The fluid now flows back through the flow channel 24 and piercing instrument into the container 26. Flow of the fluid in this direction continues until the lower optical path 32 senses a low fluid level. The process is then again reversed and repeated. Each reciprocal passing of the fluid over the filter membrane causes a filtrate to pass through the membrane where it is dispensed through the output port 22. The cycle is repeated several times to produce a desired volume of filtrate.

The amount of filtrate is dependent on the specimen volume, the membrane surface area and the number of reciprocating filtration cycles. The range, however, is limitless, from micro liters to liters.

Figure 5:
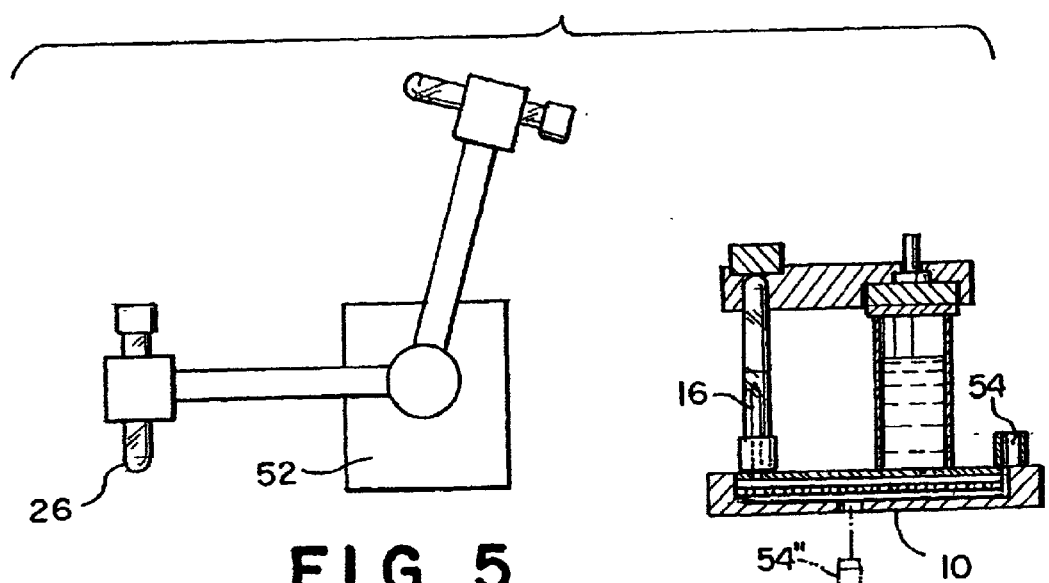
FIG. 5 is a schematic illustration showing the sequence of operation for automated microfiltration.

FIG. 5 illustrates the sequence of operation in a preferred automated system As illustrated, a specimen tube 26 is grasped by a clamp 50. The specimen is picked up, rocked by mechanism 52 to mix the fluid within tube 26, and then inverted. The mechanism 52, which may be any automated apparatus such as a robotic arm or similar device, and operated either manually or by computerized control or other control system, places the specimen tube 26 onto the specimen cell 10 by driving it down over the piercing instrument 16. The filtration process then proceeds as in the manner described in respect to FIGS. 4A, 4B and 4C. Upon completion of the filtration process, the sample may be collected in a side mounted collection cuvette such as cuvette 54 or a collection cuvette 54" positioned below the cell 10 (shown in phantom in FIG. 5) which is removed from the filtration cell 10 and transported to the appropriate instrument for analysis.

Initial testing of a system operating in accordance with the foregoing indicates that the time for the machinery to pick a container 26, such as a conventional specimen tube, and place the specimen tube is about 10 seconds. Adding the filtration cycle time of about 17 to 20 seconds, the total time to obtain a volume of filtrate sufficient for analysis is of less than 30 seconds. This is about one-half the time it took to complete the previous process.

An advantage of the apparatus and method thus described is that it need not necessarily be used with relatively complex batch microfiltration equipment. The unit or filtration module preferably includes a filtration cell in accordance with the invention, a suitable printed circuit board for process control, a standard power supply, an air reservoir and a filter head, such as the filter head described herein. The printed circuit board, power supply and air reservoir as well as the filter head can be designed in accordance with those available or known to those skilled in the art or to be developed, provided the filter head can accommodate the alternative designs described herein. The unit or filtration module can be made relatively small, (approximately 12 inches by 8 inches by 12 inches high) and is inexpensive to manufacture. This means several units can be placed together in a small area for high throughput. The units can also be used individually. For example, a unit may be portable and battery operated. This allows for its use in an operating suite, in emergency vehicles, or remote locations.

Use in an emergency vehicle allows the plasma for blood analysis to be prepared by the time the patient arrives at the hospital. When used at remote locations, the plasma can be prepared and frozen for shipment. In an operating suite, the unit can be used to prepare a sufficient quantity of plasma to help stop the patient from bleeding. As hereinafter explained, there is an existing method of mixing plasma and clotting agents, and then applying this mixture to the patient's sutured wound. The mixture helps stop postoperative bleeding.

Referring now to FIGS. 6 and 7, there is shown a microfiltration cell 10' with a well 42 for receiving a filtrate. The well 42 is filled from the bottom As illustrated in FIG. 5, plasma or other filtrate may be dispensed through a bottom outlet port 22 into the top of a well. That well may take the form of a well on a slide. See, for example, the wells 82 on the slide 76 in U.S. Pat. No. 5,000,923. A problem with trapped air arises, however, when an open well is filed from the top by a relatively viscous filtrate such as plasma. The same problem does not occur in a closed system. Depending on how the drops of filtrate fill the well, there is a chance that air can be trapped under the filtrate or plasma. In certain automated analyzers, the instrument aspirates a measured portion of the sample to a test cuvette. If air is aspirated, the instrument cannot sense the filtrate and the volume dispensed is inaccurate.

Bottom fill causes the filtration to fill the well from the bottom up. The result is the plasma or other viscous filtrate remains as a unified drop as it fills the well. Thus no air is trapped in the filtrate within the well.

FIG. 6 illustrates a filtration cell 10' having a well 42 that fills from the bottom up. The cell 40 includes a reservoir 12' mounted on a support 14'. The reservoir 12' is opened at the top, and an opening in the support 14' is also provided. A flow channel 24' is provided in the bottom of the support 14'. Mounted below the support 14' prime is a base 20'. As previously noted, the base 20' may take the form of a base such as is disclosed in U.S. Pat. No. 5,000,923. The base 20' includes channels which guide the filtrate passing through the membrane 18', to the well 42. Specifically, the filtrate is directed to the well through an opening 45 in the bottom of the well 44 flows through a filtrate channel 44 into the bottom opening of well 42. The filtrate channel 44 is closed by a cover 46 adhered to the base 20' by a pressure sensitive adhesive. A filtration cell with a bottom fill well such as is illustrated in FIGS. 6 and 7, has an additional advantage over the direct sampling filtration cell illustrated in FIGS. 2, 3 and 4. The design has two molded parts plus the microporous membrane and a die cut plastic sheet. As a consequence, the cell has less molded parts, and assembly is easier because it is only necessary to align the outer edges of the cover to the base.

Bottom up fill has especial applicability when working with small volumes of filtrate, particularly volumes measured in microliters delivered into a well of comparable size. Moreover, bottom up fill allows for use of a variety of fluids since the variations in viscosity do not affect performance of the filtering process and delivery to the collection well.

Although the present invention is primarily intended for separating plasma from blood, it is not so limited. It may be used for other biological fluids such as urine or serum. Or it may be used generally where direct transfer of a fluid from a container to the filtration apparatus is desirable.

It will be appreciated by those skilled in the art that changes could be made to the embodiments described above without departing from the broad inventive concept thereof It is understood, therefore, that this invention is not limited to the particular embodiments disclosed, but it is intended to cover modifications within the spirit and scope of the present invention as defined by the appended claims.

What is claimed is:

1. A process for directly transferring fluid to be filtered from a fluid container to a filtration cell, comprising:
   (a) providing a filtration cell comprising a reservoir, a filter membrane operatively associated with an opening in the reservoir, a base configured to receive filtrate passing through the membrane, the base including a path through which the filtrate is guided to an outlet from the filtration cell, a piercing instrument adapted to pierce a container holding the fluid to be filtered, the piercing instrument including a hollow interior in fluid communication with both the reservoir and an interior of a pierced container, and a flow channel extending between the piercing instrument and the reservoir, the flow channel being open to the filter membrane,
   (b) providing a container holding a quantity of fluid to be filtered,
   (c) piercing the container with the piercing instrument,
   (d) providing an airtight connection between the reservoir and a source of air,
   (e) alternately pressurizing the reservoir with air, and then releasing the air pressure from the filtration cell such that the fluid reciprocally flows across the filter membrane, and
   (f) collecting the filtrate from the membrane.

2. The process according to claim 1, further comprising withdrawing the piercing instrument once sufficient filtrate is collected.

3. The process according to claim 1, wherein step (f) further comprises collecting the filtrate in a well.

4. The process according to claim 3, further comprising directing the filtrate into the well through an opening in a bottom of the well.

5. The process according to claim 3, further comprising collecting the filtrate from the filter in the well, and optically monitoring the level of the filtrate in the well to determine when the level reaches a predetermined level.

6. The process according to claim 3, wherein the well is filled through an opening in the bottom when collecting filtrate measured in microliter volumes.

7. The process according to claim 1, further comprising optically monitoring the level of fluid in the reservoir and providing a signal indicating when the level of fluid in the reservoir exceeds a maximum or minimum level.

8. The process according to claim 1, wherein the fluid to be filtered is blood.

9. The process according to claim 1, wherein the filter membrane is a microporous filter membrane.

10. The process according to claim 1, wherein the filtration cell further comprises a second reservoir in fluid communication with the flow channel between the reservoir and the piercing instrument, step (d) further comprises providing an airtight connection between the second reservoir and the source of air, and step (e) further comprises alternately (i) blocking the flow of air into the reservoir, pressurizing the second reservoir with air, and venting the reservoir to release the air pressure and (ii) blocking the flow of air to the second reservoir, pressurizing the reservoir with air, and venting the second reservoir such that the fluid to be filtered flows initially from the initially from the container to the reservoir then reciprocally from the reservoir to the second reservoir across the filter membrane.

11. The process according to claim 10, wherein the filtration cell further comprises an air inlet port having a passageway therethrough and adapted to receive air from a pressure source, and the method further comprises pressurizing the container after fluid to be filtered is initially transferred to the reservoir to ensure that a substantial amount of the fluid flows from the container to the reservoir.

12. The process according to claim 1, wherein steps (b) and (c) further comprise providing a container to the piercing point to be pierced using an automated system.

13. The process according to claim 12, wherein the automated system comprises an apparatus which rocks the container prior to providing the container to the piercing point.

* * * * *

UNITED STATES PATENT AND TRADEMARK OFFICE
CERTIFICATE OF CORRECTION

PATENT NO. : 6,740,240 B2
DATED : May 25, 2004
INVENTOR(S) : Coville et al.

It is certified that error appears in the above-identified patent and that said Letters Patent is hereby corrected as shown below:

Title page,
Item [56], References Cited, OTHER PUBLICATIONS, "Microtainer ® Stat Plasma Tubes Product Brochure" reference, delete "Diff-Sale® Blood Dispenser" and insert therefor -- Diff-Safe® Blood Dispenser --. therefor,
"Microtainer ® Stat Plasma Tubes Product Brochure" reference, delete "Diff-Sale® Advertisement" and insert therefor -- Diff-Safe® Advertisement --.

Column 16,
Line 22, after the first instance of the phrase "initially from the", delete "initially from the".

Signed and Sealed this

Eighth Day of February, 2005

JON W. DUDAS
*Director of the United States Patent and Trademark Office*